US010548677B2

(12) United States Patent
Namiki

(10) Patent No.: US 10,548,677 B2
(45) Date of Patent: Feb. 4, 2020

(54) MEDICAL MANIPULATOR SYSTEM, CONTROL DEVICE OF MEDICAL MANIPULATOR SYSTEM, AND CONTROL METHOD OF MEDICAL MANIPULATOR SYSTEM

(71) Applicant: OLYMPUS CORPORATION, Tokyo (JP)

(72) Inventor: Hirotaka Namiki, Tokorozawa (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/007,150

(22) Filed: Jun. 13, 2018

(65) Prior Publication Data

US 2018/0289435 A1 Oct. 11, 2018

Related U.S. Application Data

(63) Continuation of application No. PCT/JP2015/085176, filed on Dec. 16, 2015.

(51) Int. Cl.
*G06F 19/00* (2018.01)
*A61B 34/37* (2016.01)
(Continued)

(52) U.S. Cl.
CPC .......... *A61B 34/37* (2016.02); *A61B 1/00006* (2013.01); *A61B 1/00009* (2013.01);
(Continued)

(58) Field of Classification Search
CPC . A61B 17/0469; A61B 17/29; A61B 1/00006; A61B 1/00009; A61B 1/00045;
(Continued)

(56) References Cited

U.S. PATENT DOCUMENTS

2015/0051732 A1* 2/2015 Grygorowicz ............. B25J 1/02
700/257
2018/0035054 A1* 2/2018 Sugie ................. H04N 5/23287
(Continued)

FOREIGN PATENT DOCUMENTS

JP 2001-145639 A 5/2001
JP 2003-340752 A 12/2003
(Continued)

OTHER PUBLICATIONS

International Search Report dated Mar. 1, 2016 issued in PCT/JP2015/085176.

*Primary Examiner* — Harry Y Oh
(74) *Attorney, Agent, or Firm* — Scully, Scott, Murphy & Presser, P.C.

(57) ABSTRACT

A medical manipulator system includes a slave manipulator, a master manipulator receiving a manipulation information from an operator; a driver generating a driving force for operating the slave manipulator; a processor; and a master-manipulator-side detector disposed at the master manipulator and detecting the manipulation information. The processor generates an operating command based on the manipulation information and transmits the operating command to the driver, the processor determines whether a blur information is included in the manipulation information. When the processor determines that the blur information is not included in the manipulation information, the processor stops transmitting the operating command to the driver, and when the processor determines that the blur information is included in the manipulation information, the processor removes the blur information from the manipulation information, and generates the operating command based on the manipulation information with the blur information being removed.

11 Claims, 5 Drawing Sheets

(51) Int. Cl.
*A61B 34/00* (2016.01)
*A61B 1/00* (2006.01)
*A61B 1/005* (2006.01)
*A61B 17/04* (2006.01)
*A61B 17/29* (2006.01)
*A61B 1/045* (2006.01)
*A61B 17/00* (2006.01)

(52) U.S. Cl.
CPC ........ *A61B 1/0052* (2013.01); *A61B 17/0469* (2013.01); *A61B 17/29* (2013.01); *A61B 34/25* (2016.02); *A61B 34/74* (2016.02); *A61B 1/045* (2013.01); *A61B 2017/00075* (2013.01); *A61B 2017/00398* (2013.01)

(58) Field of Classification Search
CPC . A61B 1/00149; A61B 1/0016; A61B 1/0052; A61B 1/045; A61B 2017/00075; A61B 2017/00398; A61B 2034/742; A61B 34/25; A61B 34/37; A61B 34/74; A61B 34/75; A61B 90/00; B25J 3/04; B25J 9/1689

See application file for complete search history.

(56) References Cited

U.S. PATENT DOCUMENTS

2018/0045934 A1\* 2/2018 Sugie ................. H04N 5/23212
2018/0059513 A1\* 3/2018 Ikeda ................. H04N 5/23264

FOREIGN PATENT DOCUMENTS

| JP | 4176126 B2 | 11/2008 |
| JP | 2011-206180 A | 10/2011 |
| JP | 2012-513845 A | 6/2012 |
| JP | 2015-024026 A | 2/2015 |
| JP | 2015-511544 A | 4/2015 |
| WO | WO 2010/078344 A1 | 7/2010 |

\* cited by examiner

MEDICAL MANIPULATOR SYSTEM, CONTROL DEVICE OF MEDICAL MANIPULATOR SYSTEM, AND CONTROL METHOD OF MEDICAL MANIPULATOR SYSTEM

This application is a continuation application based on a PCT International Application No. PCT/JP2015/085176, filed on Dec. 16, 2015. The content of the PCT International Application is incorporated herein by reference.

BACKGROUND OF THE INVENTION

Field of the Invention

The present invention relates to a medical manipulator system, a control device of a medical manipulator system, and a control method of a medical manipulator system.

Description of Related Art

A medical manipulator system having a slave manipulator which is disposed near an operating table and a master manipulator which is operated by a surgeon is known (For example, as disclosed in Japanese Patent Publication No. 4176126, Published Japanese Translation No. 2012-513845 of the PCT International Publication, Japanese Unexamined Patent Application, First Publication No. 2001-145639, Published Japanese Translation No. 2015-511544 of the PCT International Publication, and Japanese Unexamined Patent Application, First Publication No. 2011-206180). In the medical manipulator system, an end effector such as an endoscope, a treatment device and the like is attached to the slave manipulator. The surgeon can perform a surgery on a patient lying on the operating table by operating the master manipulator to move joints, the endoscope, and the treatment device attached to the slave manipulator.

An arm of the slave manipulator holding the end effector is configured to operate under the control of a control unit based on an operation instruction input at an operation portion of the master manipulator. However, for example, in a situation of exchanging the treatment device attached to the arm, an operation state of the master manipulator can be switched at the control unit such that an operator or an assistant can directly contact with the arm to move the treatment device.

SUMMARY OF THE INVENTION

According to a first aspect of the present invention, a medical manipulator system includes a slave manipulator including an end effector; a master manipulator configured to receive a manipulation information from an operator; a driver configured to generate a driving force for operating the slave manipulator; a processor connected to the master manipulator and the slave manipulator; and a master-manipulator-side detector disposed at the master manipulator, the master-manipulator-side detector being configured to detect the manipulation information input to the master manipulator by detecting a movement of the master manipulator, wherein the processor is configured to generate an operating command based on the manipulation information and transmit the operating command to the driver, wherein the processor is configured to determine whether a blur information due to a camera shake by the operator is included in the manipulation information input to the master manipulator based on a detection result by the master-manipulator-side detector, wherein when the processor determines that the blur information is not included in the manipulation information, the processor is configured to stop transmitting the operating command to the driver, and wherein when the processor determines that the blur information is included in the manipulation information, the processor is configured to remove the blur information from the manipulation information, and the processor is configured to generate the operating command based on the manipulation information with the blur information being removed.

According to a second aspect of the present invention, in the medical manipulator system according to the first aspect, the slave manipulator may further include a slave arm, the slave arm being configured to hold the end effector, and the slave arm being configured to operate based on the manipulation information input to the master manipulator; and a slave-manipulator-side detector disposed at the slave arm, the slave-manipulator-side detector being configured to detect the blur information, wherein the processor is configured to switch between a driving mode and a freely moving mode, in the driving mode, the processor is configured to control an operation of the slave arm by operating the slave arm based on the driving force from the driver, and when the blur information is detected by the slave-manipulator-side detector, the processor is configured to switch from the driving mode to the freely moving mode in which the slave arm is movable by another force except for the driving force.

According to a third aspect of the present invention, in the medical manipulator system according to the first aspect, the processor maybe configured to include a plurality of control modes, and when the blur information is not detected, the processor may be configured to stop an update of the operating command to the driver based on a manipulation information from which the blur information is not detected and maintain a current control mode among the plurality of control modes.

According to a fourth aspect of the present invention, in the medical manipulator system according to the first aspect, the processor maybe configured to include a plurality of control modes, wherein when the blur information is not detected, the processor may be configured to stop transmitting the operating command to the driver and prompt the operator to select a next control mode among the plurality of control modes, and wherein when the next control mode has been selected and the blur information is detected, the processor is configured to switch to the next control mode.

According to a fifth aspect of the present invention, in the medical manipulator system according to the first aspect, the processor maybe configured to include a plurality of control modes, wherein when the blur information is not detected, the processor may be configured to stop transmitting the operating command to the driver and prompt the operator to select a next control mode among the plurality of control modes, and wherein when the next control mode has been selected and the blur information is detected, the processor may be configured to switch to the next control mode.

According to a sixth aspect of the present invention, a control method of a medical manipulator system is provided, the medical manipulator system including a slave manipulator having an end effector; a master manipulator receiving a manipulation information from an operator; a driver generating a driving force for operating the slave manipulator; a processor connected to the master manipulator and the slave manipulator and configured to generate an operating command based on the manipulation information and transmit the operating command to the driver; and a master-manipulator-side detector disposed at the master manipulator and configured to detect the manipulation information input to the master manipulator by detecting a movement of the master manipulator, the control method of a medical manipulator system including a step of determining whether a blur information due to a camera shake by the operator is included in the manipulation information; a step of stopping transmitting the operating command to the driver, when the blur information is determined not to be included in the manipulation information; a step of removing the blur information from the manipulation information, and a step of generating the operating command based on the manipulation information with the blur information being removed, when the blur information is determined to be included in the manipulation information.

According to a seventh aspect of the present invention, the slave manipulator further includes a slave arm configured to hold the end effector and operate based on the manipulation information input to the master manipulator; and a slave-manipulator-side detector disposed at the slave arm and configured to detect the blur information, the control method of a medical manipulator system according to the sixth aspect may further include a step of controlling an operation of the slave arm by operating the slave arm based on the driving force from the driver, and a step of freely moving the slave arm by another force except for the driving force, when the blur information is detected by the slave-manipulator-side detector.

According to an eighth aspect of the present invention, the control method of a medical manipulator system according to the sixth aspect may further include a step of stopping an update of the operating command to the driver based on a manipulation information from which the blur information is not detected and maintaining a current state of the medical manipulator system, when the blur information is not detected.

According to a ninth aspect of the present invention, the control method of a medical manipulator system according to the sixth aspect may further include a step of stopping transmitting the operating command to the driver, and prompting the operator to select a next step, when the blur information is not detected, and a step of switching to the next step that is selected by the operator, when the blur information is detected after the next step is selected.

According to a tenth aspect of the present invention, the control method of a medical manipulator system according to the sixth aspect may further include a step of removing a specified frequency component from an amount of the manipulation information detected by the master-manipulator-side detector, wherein the step of determining whether the blur information is included in the manipulation information is processed by comparing the amount of the manipulation information before removing the specified frequency component and the amount of the manipulation information after removing the specified frequency component.

According to an eleventh aspect of the present invention, a control device of a medical manipulator system is provided, the medical manipulator system including a slave manipulator having an end effector, a master manipulator receiving a manipulation information from an operator, a driver generating a driving force for operating the slave manipulator, and a master-manipulator-side detector disposed at the master manipulator and configured to detect the manipulation information input to the master manipulator by detecting a movement of the master manipulator, the control device of a medical manipulator system including a processor configured to generate an operating command based on the manipulation information detected by the master-manipulator-side detector and transmit the operating command to the driver of the slave manipulator, wherein the processor is configured to determine whether a blur information due to a camera shake by the operator is included in the manipulation information, wherein when the blur information is determined not to be included in the manipulation information, the processor is configured to stop transmitting the operating command to the driver, and wherein when the blur information is determined to be included in the manipulation information, the processor is configured to remove the blur information from the manipulation information and generate the operating command based on the manipulation information with the blur information being removed.

DETAILED DESCRIPTION OF THE INVENTION

Figure 1:
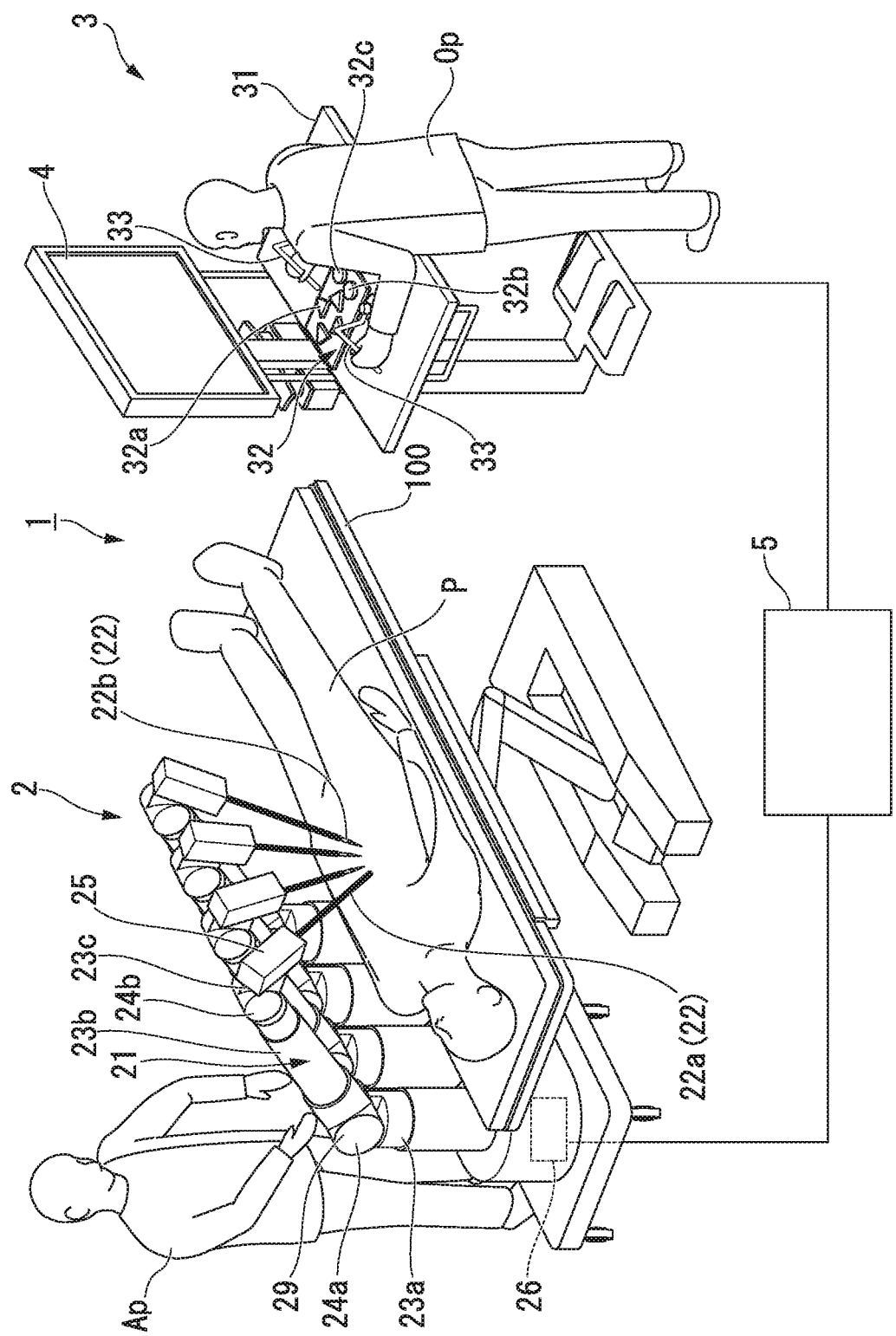
FIG. 1 is perspective view showing a medical manipulator system according to an embodiment of the present invention.
Figure 2:
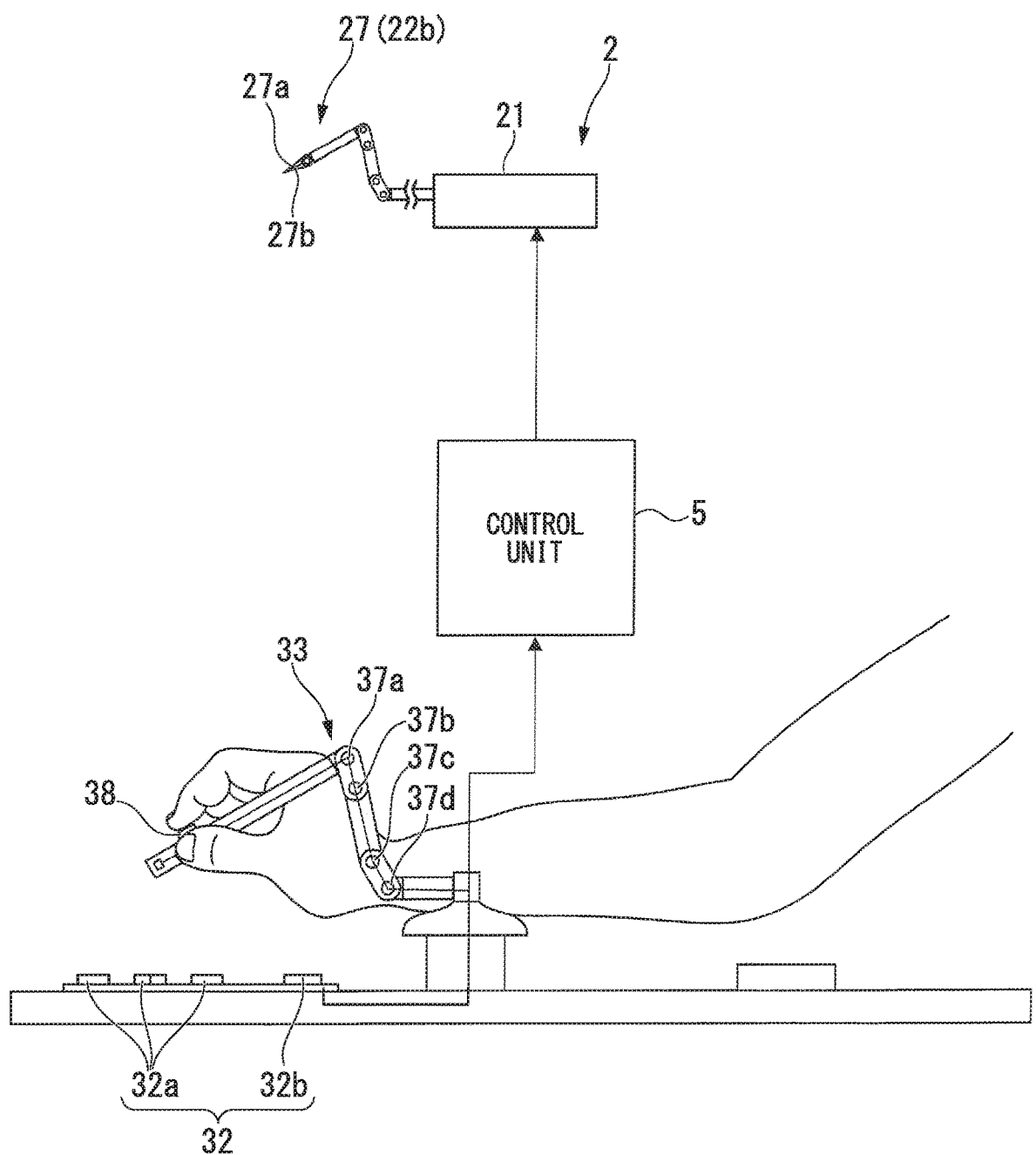
FIG. 2 is a schematic diagram showing an example of an operation portion of the medical manipulator system according to the present embodiment.

A medical manipulator system according to an embodiment of the present invention will be described. FIG. 1 is a perspective view showing the medical manipulator system 1 according to the present embodiment. FIG. 2 is a schematic diagram showing an example of an operation portion of the medical manipulator system 1 according to the present embodiment. The medical manipulator system 1 according to the present embodiment (hereinafter described as "a manipulator system") is a master-slave type medical manipulator system used in a surgery. The manipulator system 1 is a system configured to remotely control a slave arm 21 so as to cause the slave arm 21 to follow the operation of the master arm. In the following description, a proximal end side is defined as a side of the operation portion in the master manipulator 3, and a distal end side is defined as a side of an end effector 22 closer to the patient P placed on the operating table 100.

As shown in FIG. 1, the manipulator system 1 includes a slave manipulator 2, the master manipulator 3, a display apparatus 4 and a control unit (processor) 5.

The slave manipulator 2 is disposed near the operating table 100. The slave manipulator 2 includes a plurality of slave arms 21, a plurality of end effectors 22, and a plurality of driving portions (drivers) 26. Since each of the plurality of slave arms 21 has the same configuration, one of the plurality of slave arms 21 will be described as an example.

The slave arm 21 includes a plurality of multi-degree freedom joints configured by connecting a plurality of axial portions 23a, 23b, 23c with each other at slave joint portions 24a, 24b. The slave arm 21 is configured to be operatable in multiple axes. Each of the plurality of multi-degree freedom joints is individually driven by the driving unit 26.

The slave arm 21 further includes an attachment portion 25. The attachment portion 25 is provided to configure a distal end portion of the slave arm 21, and the end effector 22 is attached to the attachment portion 25. The attachment portion 25 is rotatably attached to the axial portion 23c at the distal end of the slave arm 21.

The end effector 22 is detachably connected to the attachment portion 25. A distal end portion of the end effector 22 is inserted into the inside of the body of the patient P so as to be used for observing the treatment target sites and treating the treatment target sites. The end effector 22 includes an endoscope 22a and a treatment device 22b. The endoscope 22a includes an imaging portion having an image sensor. The treatment device 22b may be a treatment portion configured to dissect or suture the treatment target sites, or a grasping portion configured to grasp tissues at the treatment target sites. The treatment device 22b is suitably selected from several variations and attached based on the treatment details of the surgery. The configuration of the end effector 22 is not particularly limited.

For example, as shown in FIG. 2, the treatment device 22b according to the present embodiment is a grasping forceps 27 configured to be able to grasp the tissues. The grasping forceps 27 includes a pair of forceps pieces 27a, 27b configured to be able to open and close. The pair of forceps pieces 27a, 27b are connected to the driving unit 26 (See FIG. 1) by a wire (not shown), and the pair of forceps pieces 27a, 27b are operated by a force transmitted from the driving unit 26. The pair of forceps pieces 27a, 27b are configured to operate based on an operating instruction which is issued by the control unit 5 and transmitted to the driving unit 26, wherein the operating instruction corresponds to an operation with respect to an operation arm 33 by the operator that will be described later.

Figure 3:
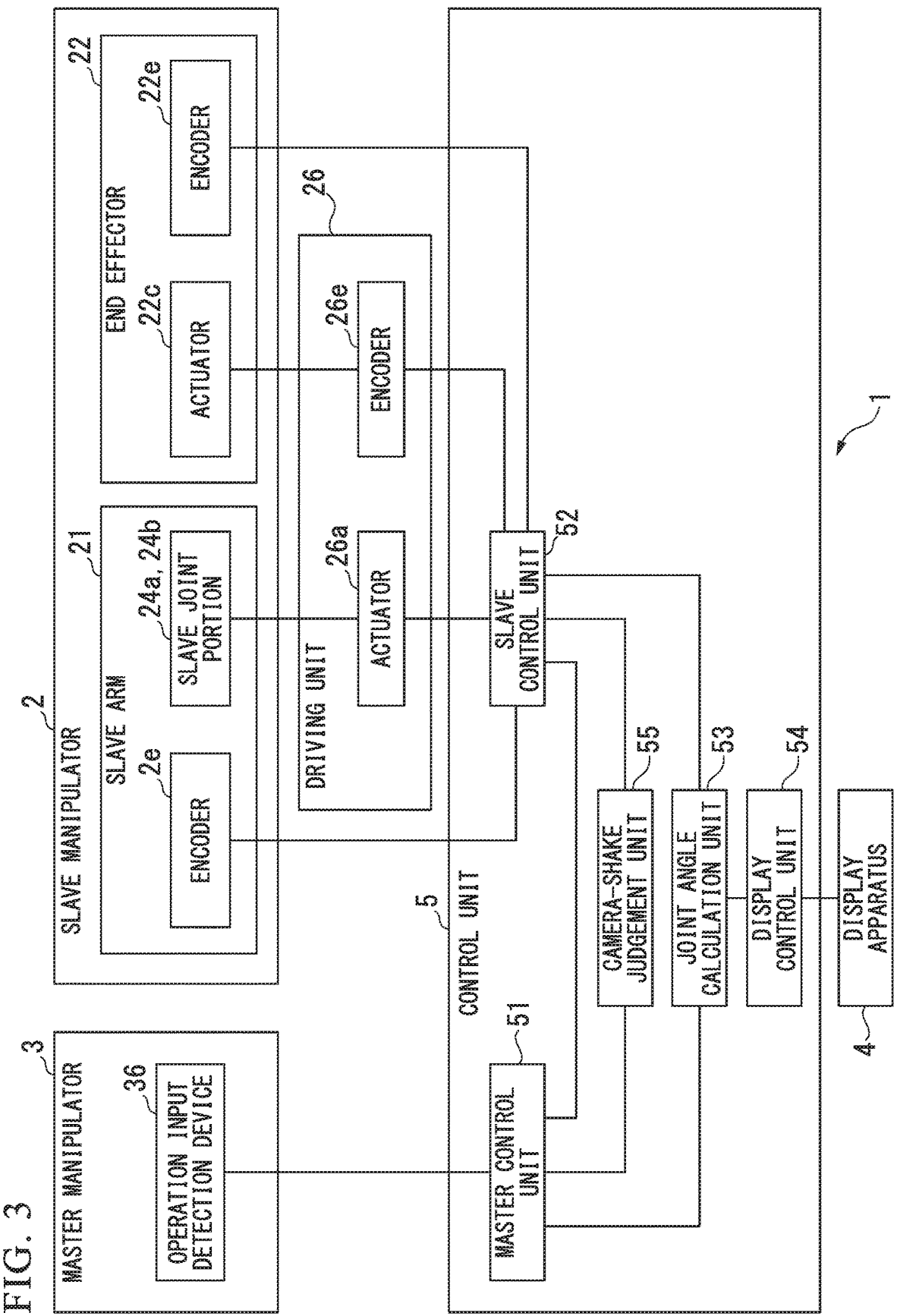
FIG. 3 is a block diagram showing the medical manipulator system according to the present embodiment.

FIG. 3 shows a block diagram of the manipulator system 1. The driving unit 26 is disposed on the slave manipulator 2. For example, the driving unit 26 is configured by a plurality of actuators 26a, and the plurality of actuators 26a are connected with each other via a driving transmission member (not show) that is inserted through the plurality of axial portions of the slave manipulator 2. The driving unit 26 is configured to generate a driving force used for driving the plurality of actuators 26a and thus operating the slave joint portions 24a, 24b based on the operating instruction issued by the control unit 5. The driving unit 26 includes an encoder 26e configured to detect a movement of the actuators 26a. The slave arm 21 is configured to be movable following a control signal from a slave control portion that is described later via the driving unit 26 and the driving transmission member (not shown). For example, the actuators 26a can be configured by a servomotor including an incremental encoder, a reduction drive, and the like.

In the driving unit 26, the end effector 22 is configured to be operable. The driving unit 26 is connected with an actuator 22c configured to drive the end effector 22. For example, in the situation when the grasping forceps 27 is attached to the attachment portion 25 to be used as the end effector 22, the driving unit 26 operates the pair of forceps pieces 27a, 27b of the grasping forceps 27 by a wire-driven mechanism following an operation of the operation arm 33 that will be described later. A movement amount of the end effector 22 is determined by the encoder 22e and the movement amount is transmitted to a slave control unit 52. The slave control unit 52 repeats control of transmitting control signals to the driving unit 26, wherein the control signals are generated based on the movement amounts detected by the encoder 22e.

The master manipulator 3 is configured to transmit the operation input (manipulation information) by the operator Op to the slave manipulator 2. As shown in FIG. 1, the master manipulator 3 includes an operation console 31, a button operation unit 32, and an operation arm 33.

The operation console 31 is attached to the display apparatus 4. The display apparatus 4 is configured to display the image captured by the endoscope 22a and the information necessary for the operation of the manipulator system 1 according to the present embodiment. The display apparatus 4 is connected to the control unit 5 and the display apparatus 4 is configured to display the video based on the video signal output by the control unit 5. The configuration of the display apparatus 4 is not particularly limited.

The button operation unit 32 is configured on the top surface of the operation console 31. The button operation unit 32 includes a moving button 32a, an operation-switching button 32b, and a determination button 32c, and the button operation unit 32 is operated by the operator Op. The moving button 32a is formed by four buttons configured to move the slave arm 21 in the up/down directions and the left/right directions (the X axis direction, the Y axis direction). The operation-switching button 32b is configured to select the operation target of the moving button 32a. The determination button 32c is configured to be operated when the necessary operation instruction such as the control mode and the like is determined from the information necessary for the operation that is displayed on the display apparatus 4.

The operation arm 33 is the operation unit configured for the operation of the end effector 22. The operation arm 33 is formed in a shape corresponding to the movement of the end effector 22, and the operation arm 33 is configured to instruct the operation of the end effector 22 and the driving of the driving unit 26. The control unit 5 is configured to control the end effector 22 to move in the same manner as the movement of the operation arm 33, when the operator Op operates and moves the operation arm 33.

The button operation unit 32 and the operation arm 33 form the operation unit. The input relating to the movement of the slave arm 21 is performed at the button operation unit 32, and the operation input for moving the end effector 22 is performed at the operation arm 33. As shown in FIG. 3, an operation-input detection device (operation-unit-side detection device) 36 is provided at the operation unit.

As shown in FIG. 3, the control unit 5 includes a master control unit (processor) 51, a slave control unit (processor) 52, a joint angle calculation unit 53, a display control unit 54, and a blur determination unit 55. The control unit 5 is connected to the slave manipulator 2 and the master manipulator 3. The control unit 5 is configured to convert the input at the operation unit of the master manipulator 3 into the control signal of the driving unit 26, and the control unit 5 is configured to transmit the control signal to the driving unit 26 to drive the driving unit 26.

The master control unit 51 is configured to detect the operation of the operator Op to the operation unit (the button operation unit 32 and the operation arm 33) of the master manipulator 3 as shown in FIG. 1 by each operation-input detection device 36. The detection result of the operation input by each operation-input detection device 36 is output to the master control unit 51 as the operation input information. The master control unit 51 is configured to generate a predetermined driving unit operation signal for operating the driving unit 26 based on the operation input information and transmit the driving unit operation signal to the slave control unit 52.

The master control unit 51 is configured to determine whether a blur due to the shaking of the hand of the operator Op (camera shake) occurs according to the output amount of the operation input information from each operation-input detection device 36. The output amount of the operation input information from each operation-input detection device 36 changes depending on the occurrence of the blur since the blur occurs during the hand operation of the operator Op during the operation input. For example, when the operator Op operates the button operation unit 32, a slight shaking (blur) of the finger pressing the button occurs. On the other hand, in a situation when the arm of the operator Op and the like unintentionally contacts with the button, compared with the blur occuring in the situation of the finger intentionally pressing the button, the same shaking does not occur. Furthermore, in a situation when the peripheral apparatus and devices disposed near the operation console 31 contact with the button operation unit 32 or the operation arm 33, each operation-input detection device 36 of the operation unit detects the occurrence of the movement in the operation unit, however, the same shaking as the blur occurring at the finger when the operator Oppresses the button does not occur. Accordingly, the master control unit 51 determines the occurrence of the blur based on the output amount of each operation-input detection device 36. Specifically, in the output amount of each operation-input detection device 36, a vibration with a predetermined frequency due to the shaking of the hand of the operator Op is included in the force applied when each button of the button operation unit 32 is pressed and the operation arm 33 is moved.

The operation-input detection device 36 can be configured as a detection device detecting the input to the button operation unit 32 by a force sensor, a detection device detecting the input to the button operation unit 32 that is configured from the buttons (icons) displayed on a touch panel as a positional touch signal and a force touch signal, and a detection device detecting the input to the operation arm 33 using a force sensor, an acceleration sensor, or an angle sensor and the like.

The blur determination unit 55 is configured to perform the blur determination process of judging the occurrence of the blur based on a difference between the output amount (operation input amount) of each operation-input detection device 36 before the filtering process and the output amount (operation input amount) of each operation-input detection device 36 after the filtering process, wherein the filtering process is performed by using a notch filter or a band-pass filter and the like. For example, the occurrence of the blur can be determined by using the gain, the duration time and the like of the frequency band corresponding to the occurrence of the blur.

In a situation when the blur determination unit 55 determines that the blur existed in the operation input in the blur determination process, the master control unit selects the control mode based on the operation input. The control modes of the master control unit 51 do not only include a control mode of driving the slave arm 21 based on the operation input at the operation unit, but also include another control mode such as an operation-switching mode of selecting the operation target elements (such as the slave joint 24a, 24b of one of the plurality of slave arms 21, the end effector 22, and the like) at the operation unit by the operator Op.

Here, the phrase "operation input" does not only mean the input when the operation unit is operated intentionally by the operator Op, but also means unintentional input by the operator Op. For example, unintentional input by the operator Op can be considered as the situation when part of the body of the operator Op (for example, the arm) contact with the operation unit, or the situation when other devices contacts with the operation unit. Furthermore, the situation when the operator Op, the assistant Ap, the peripheral devices and the like contact with the slave arm 21 and move the slave arm 21 also means unintentional input.

Accordingly, in the manipulator system 1 according to the present embodiment, in the situation when the blur occurs during the operation input, it is determined that intentional input by the operator Op is performed. On the other hand, in the situation when the blur does not occur during the operation input, it is determined that unintentional input such as the contact with the operation unit and the like exists. Specifically, the occurrence of the blur is determined at the blur determination unit 55, and the driving mode of the slave manipulator 2 is determined and set based on the result of the judgment.

When the blur determination unit 55 determines that the blur occurs during the operation input, the master control unit 51 selects an operation-input transmission mode and transmits the operation-input information (operation input amount, vector and the like) to the slave control unit 52. The slave control unit 52 drives the driving unit 26 based on the operation-input information (operation input amount, vector and the like), and the slave control unit controls each joint 24a, 24b and the end effector 22 to be movable corresponding to the operation input of the operator Op. At this time, when the master control unit 51 transmits the information generated by removing the detected amount of the blur as the operation-input information to the slave control unit 52, the cooperation precision between the operation input of the operator Op and the movement of the salve manipulator 2 and the end effector 22 is improved such that the operability is improved.

When the blur determination unit 55 determines that the blur does not occur, the master control unit 51 selects and sets an operation-input non-transmission mode to transmit a driving stoppage signal to the slave control unit 52 such that the slave control unit 52 stops the operation of the driving unit 26. As a result, when an unintentional input of the operator Op is input to the operation unit (the operation unit is moved against the intention of the operator Op), the operation of the slave manipulator 2 is stopped. That is, the slave manipulator 2 is configured to prevent itself from being operated against the intention of the operator Op.

Either, in the operation-input non-transmission mode, the new transmission of the operation input to the slave control unit 52 is stopped (withdraw update), and the operation of the driving unit 26 (existing control mode) based on the operation input transmitted from the master control unit 51 during the last control loop is maintained. That is, the slave manipulator 2 maybe configured such that the operation input is not reflected in the operation of the slave manipulator 2, when unintentional input of the operator Op is input to the operation unit (the operation unit is moved against the intention of the operator Op).

When the slave control unit 52 receives the operating instruction generated by the master control unit 51 and transmitted to the slave control unit 52, the slave control unit controls the driving unit 26 to move the slave arm 21 and the end effector 22.

The joint angle calculation unit 53 is configured to calculate the orientation of the joint of the operation unit (for example, a plurality of operation joints 37a, 37b, 37c, 37d included in the operation arm 33, as shown in FIG. 2) based on the detected movement amount and movement direction by each operation-input detection device 36. The joint angle calculation unit 53 is configured to acquire the angle information from the encoder 2e of each slave joint portion 24a, 24b disposed at the slave manipulator 2, and the joint angle calculation unit 53 is configured to calculate the angle of each slave joint portion 24a, 24b in consideration of the mechanical elements between the actuator and the end effector 22.

The joint angle calculation unit 53 includes the information for specifying a predetermined range for each treatment device as a moveable range of each joint element disposed in the joint portion of the treatment device 22b. Furthermore, the joint angle calculation unit 53 defines a shape-synchronizable range using a predetermined fixed angle range with respect to the current position of the joint portion as a reference, the predetermined fixed angle range being a movable range of each joint element disposed in the joint portion of the treatment device 22b.

The angle calculation unit 53 transmits the information indicating the angle of the joint portion of the treatment device 22b and the angle of each slave joint portion 24a, 24b of the slave arm 21, the information indicating the movable range of each joint element disposed at the joint portion of the treatment device 22b, and the information indicating the above-identified shape-synchronizable range, to the display control unit 54.

The display control unit 54 includes an image-processing circuit. The display control unit 54 is configured to generate the image information for visually transmitting to the user with the information indicating the angle of the joint portion of the treatment device 22b and the angle of each slave joint portion 24a, 24b of the slave arm 21, the information indicating the movable range of each joint element disposed at the joint portion of the treatment device 22b, and the angle of each slave joint portion 24a, 24b with respect to the angle of each joint element configuring the joint portion of the treatment device 22b based on the above-identified information indicating the shape-synchronizable range. In addition, the display control unit 54 is configured to generate an image for displaying the image data acquired from the endoscope 22a on the display apparatus 4.

Figure 4:
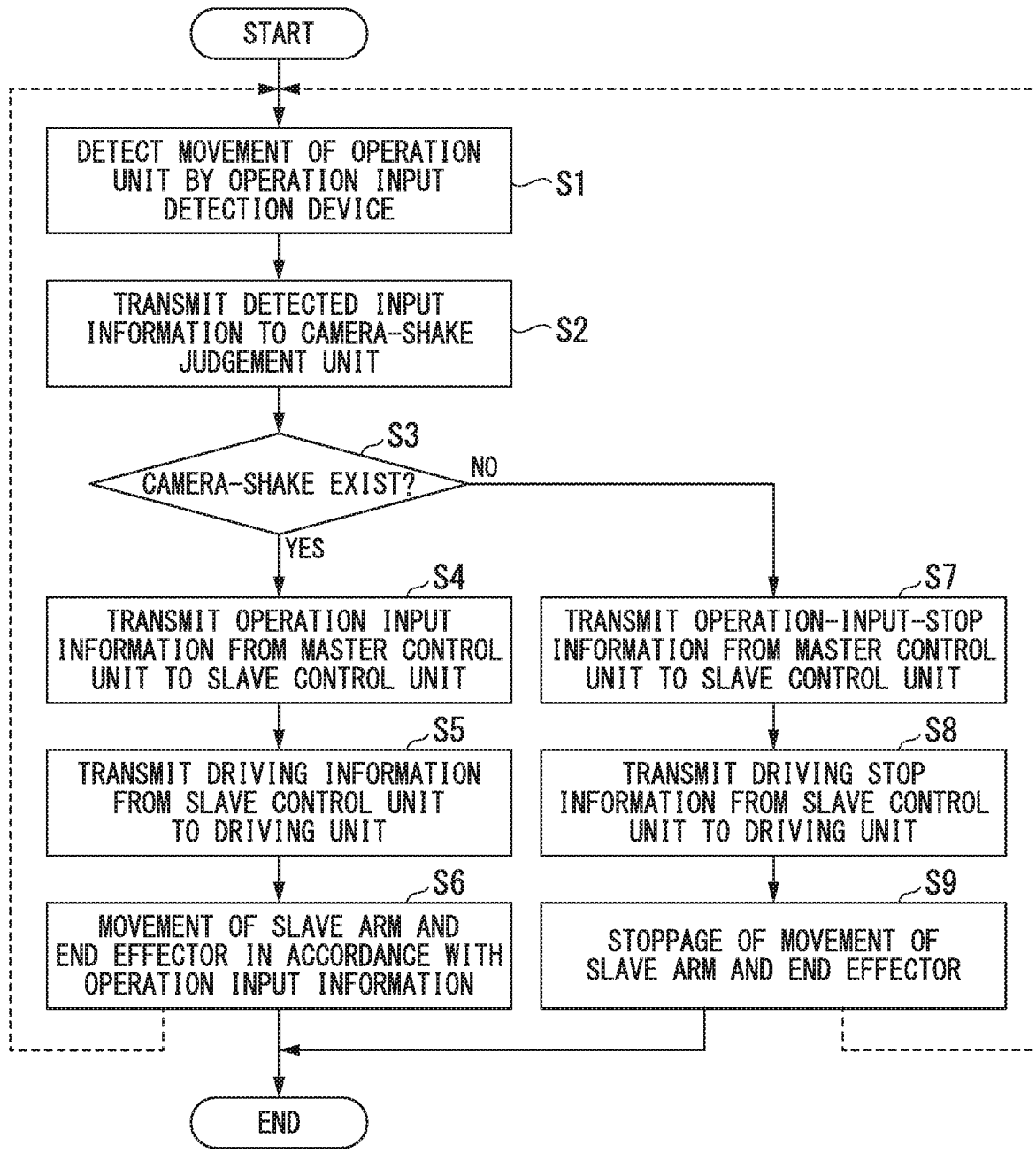
FIG. 4 is a flow chart showing procedures of the medical manipulator system according to the present embodiment.

Next, a medical manipulator control method using the manipulator system 1 according to the present embodiment will be described. FIG. 4 shows a flowchart of the process in the manipulator system 1.

The endoscope 22a and the treatment device 22b necessary for the surgery are disposed at the distal end portion of each slave manipulator 2, and each slave manipulator 2 is disposed near the operating table 100 on which the patient P is lying. The orientation of each slave joint portion 24a, 24b of the slave arm 21 is adjusted such that the slave manipulator is positioned so that the distal end portion of the end effector 22 can be disposed at a suitable position corresponding to a position instructed by the operator Op or the assistant Ap.

When an operation input is applied at one of the operation units, the operation-input detection device 36 detects the movement of the operation unit (Step S1). The operation-input detection device 36 transmits the input information with regard to the detected movement of the operation unit (including a type, a movement amount, and a movement direction of the operation unit being detected to move) to the blur determination unit 55 of the master control unit 51 (Step S2). For example, when the operator Op presses the operation-switching button 32b of the button operation unit 32, the master control unit 51 selects and sets the operation-switching mode, and the master control unit 51 causes the display control unit 54 to perform a process of displaying an image used for selecting the slave arm 21 or the end effector 22 as the operation target of the button operation unit 32 on the display apparatus 4.

In the operation-switching mode, the operator Op selects the element of the slave manipulator 2 as the operation target of the button operation unit 32 and presses the determination button 32c while watching the display apparatus 4. An example of causing the slave joint portion 24a disposed at the distal end side of the slave arm 21 at which the endoscope 22a is disposed to be movable will be described. When the operator Op presses the moving button 32a corresponding to the direction in which the slave manipulator 2 is desired to be moved, the operation-input detection device 36 transmits the direction of the pressed moving button 32a (up, down, left, and right) and the duration time when the moving button 32a is pressed to the master control unit 51.

At this time, the blur determination unit 55 of the master control unit 51 determines whether there is a blur included in the operation-input information of the moving button 32a (Step S3). In a situation in which the blur determination unit 55 determines that there is a blur included in the operation-input information of the moving button 32a (Yes), the master control unit 51 selects and sets the operation-input transmission mode. The master control unit 51 transmits the operation-input information to the slave control unit 52 (Step S4). In the operation-input transmission mode, for example, the slave control unit 52 transmits the operation-input information of the moving button 32a to the driving unit 26 (Step S5). According to the operation-input information, the driving unit 26 selects one actuator 26a configured to drive the slave joint portion 24a of the selected slave manipulator 2, from a plurality of actuators 26a included in the driving unit 26, and the driving unit 26 performs a process of driving the selected actuator 26a based on the direction of the pressed moving button 32a (up, down, left, and right) and the duration time when the moving button 32a is pressed (Step S6).

During the process from Step S4 to Step S6, when the master control unit 51 transmits the information generated by removing the detected blur amount to the slave control unit 52 as the operation-input information, the cooperation precision between the operation input of the operator Op and the movement of the slave joint portion 24a is improved such that the operability is improved.

On the other hand, in the Step S3, when the blur determination unit 55 determines that no blur occurs in the operation input (No), the master control unit 51 selects and sets the operation-input non-transmission mode so as to transmit an operation-input stoppage information to the slave control unit 52 (Step S7). When the operation-input stoppage information (driving stoppage information) is received, the slave control unit 52 transmits the driving stoppage information to the driving unit 26 (Step S8). The driving unit 26 stops the movement of the actuator 26a of the slave joint potion 24a (Step S9).

Next, the blur determination of the operation arm 33 will be described. When the operation-switching button 32b of the button operation unit 32 is pressed, the master control unit 51 selects and sets the operation-switching mode so as to perform the process of causing the display apparatus 4 to display the image used for selecting the slave arm 21 or the end effector 22 as the operation target of the button operation unit 32. The operator Op selects the operation arm 33 as the operation target. As shown in FIG. 2, when the operator Op grasps the operation arm 33, the operation-input detection device 36 detects the movement of the operation arm 33. The detected operation-input amount by the operation-input detection device 36 is transmitted to the blur determination unit 55 of the control unit 5. The blur determination unit 55 determines whether there is a blur included in the operation-input amount of the operation arm 33 by the same process as that of the button operation unit 32.

When the blur determination unit 55 determines that there is a blur included in the operation-input amount of the operation arm 33 (Yes), the same as the example of the button operation unit 32, the master control unit 51 transmits the operation-input information with respect to the distal end portion of the treatment device 22b to the slave control unit 52 (Step S4).

The slave control unit 52 transmits the operation-input information of the operation arm 33 to the driving unit 26 (Step S5). The driving unit 26 drives the actuator 22c configured to drive the treatment device 22b attached to the selected slave manipulator 2 so as to move the treatment device 22b in a similar manner as the movement of the operation arm 33 (Step S6).

On the other hand, when the blur determination unit 55 determines that the blur is not included in the operation-input amount of the operation arm 33 (No), the master control unit 51 selects and sets the operation-input non-transmission mode so as to transmit the driving stoppage information to the slave control unit 52 (Step S7). The Step S8 and the Step S9 are the same as that in the example of the button operation unit 32.

The medical manipulator control method will be further described using the example when the operator Op is operating the moving button 32a of the button operation unit 32 and the arm of the operator Op comes into contact with the operator arm 33.

At this time, the operation-input detection device 36 detects the movement of the moving button 32a and the operation arm 33. The blur determination unit 55 determines whether there is a blur included in the operation-input information of each of the moving button 32a and the operation arm 33 (Step S3).

Since the operator Op is operating the moving button 32a of the button operation unit 32, the blur determination unit 55 determines that there is a blur included in the operation-input information of the button operation unit 32, and the blur determination unit 55 performs the process from Step S4 to Step S6. On the other hand, since the blur due to the operator Op is not detected from the operation-input information of the operation arm 33, the blur determination unit 55 determines that there is not a blur included in the operation-input information of the operation arm 33, and the blur determination unit 55 performs the process from Step S7 to Step S9. That is, the manipulator system 1 is controlled such that the slave arm 21 is operated based on the operation input via the moving button 32a, however, the end effector is not operated even if an operation input of the operation arm 33 is detected. As a result, the malfunction of the slave arm 21 and the end effector 22 due to incorrect operations can be prevented.

Furthermore, for example, when the operator Op is not operating the operation unit and the peripheral devices, the used devices, or the assistant Ap unintentionally contacts with the operation unit, and the process from the above-identified Step S1 to Step S9 is performed such that the malfunction of the slave arm 21 and the end effector 22 due to incorrect operation can be prevented.

Also, the manipulator system 1 can be configured such that the process from Step S1 to Step S9 as shown in FIG. 4 is repeatedly performed during the period when the manipulator system 1 is operated.

The manipulator system 1 according to the present embodiment is configured to make it possible to avoid unexpected operations of the slave manipulator 2 due to unintentional contact with the operation unit by the surrounding objects and people such that the manipulator system 1 is stably operable.

Generally, a plurality of operation units are necessary for a multifunction manipulator system. The manipulator system 1 according to the present embodiment is configured such that only the operation input via the operation unit that is intentionally operated by the operator Op is reflected in the operation of the slave manipulator 2, and the operation input applied when the arm of the operator Op and the like contacts with other operation units by mistake is not reflected in the operation of the slave manipulator 2. Accordingly, it is possible to configure a manipulator system to prevent malfunction and to have the outstanding operability even if a plurality of operation units are provided.

In the manipulator system according to the present embodiment, the control unit determines whether an operation input is an intentional operation input by the operator Op based on the existence of the blur in the operation input. Accordingly, it is possible to provide a manipulator system that can prevent malfunction due to erroneous operation and improve the operability of the operator Op so as to realize a smooth surgery operation.

In the present embodiment, the slave arm 21 including three axial portions 23a, 23b, 23c, and two slave joint portions 24a, 24b is described as an example. However, the configuration of the slave arm 21 including the amount of the axial portions and the movable directions is not limited thereto. The slave arm 21 only has to be configured with a joint structure having one or more joint portions with at least one freedom degree, and the joint structure being configured for operating the manipulator.

In the present embodiment, the operation unit configured by the button operation unit 32 and the operation arm 33 is described as an example. However, the configuration of the operation unit is not limited thereto. The operation unit only has to be configured to be able to operate the slave arm 21 and the end effector 22. For example, the operation unit can be configured as a joystick and the like.

In the manipulator according to the present embodiment, when the blur determination unit 55 determines that the blur is not included in the operation input (the situation in which the blur is not detected), the example of stopping the operation instruction to the driving unit 26 at the master control unit 51 is described. At this time, furthermore, a control mode selection step of displaying the selectable control mode on the display apparatus 4 and making the operator Op to select any desirable control mode may be included. Furthermore, as the operator Op has selected a control mode, at the blur determination unit 55, when the blur determination unit 55 determines that the blur is included in the operation input (the situation in which the blur is detected), a control mode-switching step of switching to the control mode selected in the control mode selection step may be included.

In the present embodiment, the operation unit having one operation-input detection device 36 is described as an example. However, each of the button operation unit 32 and the operation arm 33 may include the operation-input detection device 3 6 . Also, the operation-input detection device 36 can be configured at either of the button operation unit 32 and the operation arm 33.

Modification Example

In the above-described embodiment, determining whether the intentional operation input by the operator Op exists by detecting the blur of the operator Op with respect to the operation input to the operation unit disposed at the master manipulator 3 is described as an example. However, not limited to the operation unit of the master manipulator 3, a configuration can be configured to determine whether the intentional operation input by the operator Op exists by detecting the blur of the operator Op with respect to the operation input at the side of the slave manipulator 2.

Figure 5:
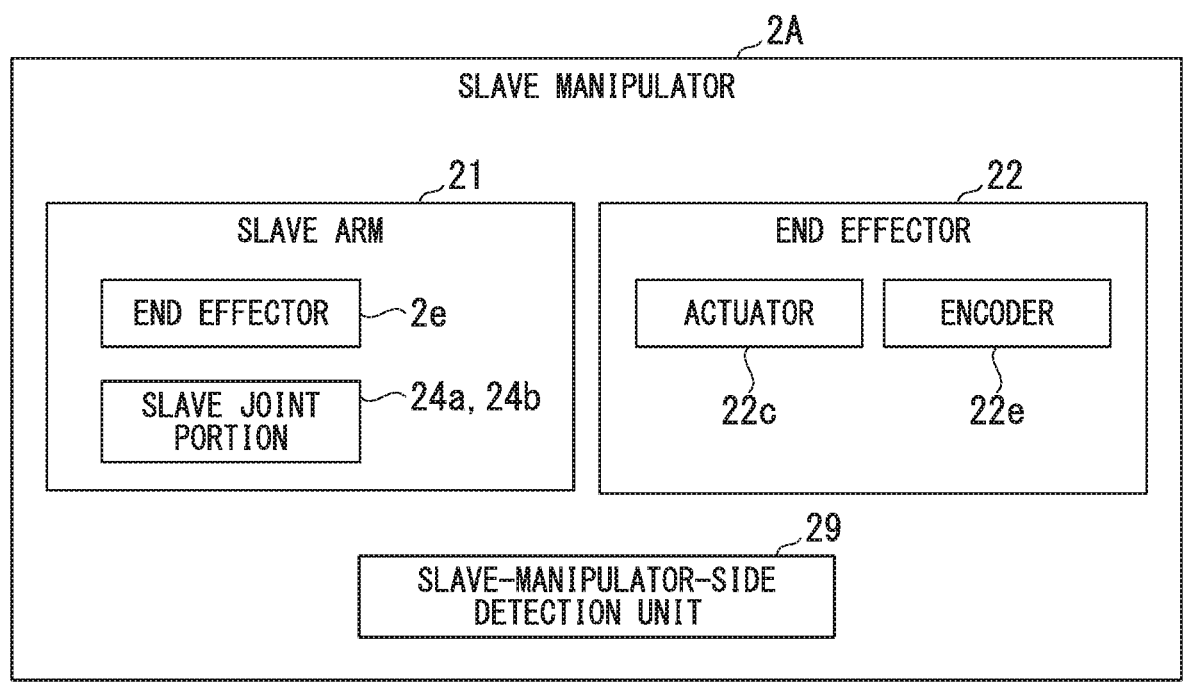
FIG. 5 is a block diagram showing a modification example of the slave manipulator.

FIG. 5 shows a block diagram of a slave manipulator 2A according to the modification example. The slave joint portions 24a, 24b are configured to be operated by the driving unit 26 based on the operation input via the operation unit. However, as shown in FIG. 1, in order to adjust the orientations and the positions of the slave arm 21 and the end effector 22, there are cases when the assistant Ap (or the operator Op) directly operates the slave arm 21 and the end effector 22. Accordingly, as shown in FIG. 5, a slave-manipulator-side detection unit 29 with the same configuration as the operation-input detection device 36 according to the above-described embodiment can be disposed at the slave arm 21, the slave joint portions 24a, 24b, and the end effector 22. The slave-manipulator-side detection unit 29 can be disposed at each of the slave arm 21, the slave joint portions 24a, 24b, and the end effector 22, or the slave-manipulator-side detection unit 29 can be only disposed at any one or a plurality of the configuration elements.

In the situation when the assistant or the operator Op intentionally contacts and operates the slave arm 21, the slave-manipulator-side detection unit 29 of the slave manipulator 2A detects the operation input and transmits the operation-input information to a slave operation unit (not shown). The operation-input information includes the information such as the place where the operation input is detected and the like.

When the slave control unit 52 receives the operation-input information of the slave manipulator 2A, the slave control unit 52 transmits the operation-input information to the blur determination unit 55. The blur determination unit 55 determines whether there is a blur included in the operation input of the slave manipulator 2A based on the operation-input information transmitted from the slave control unit 52 with the same method as that of the above-described embodiment.

When the blur determination unit 55 determines that there is a blur included in the operation input of the slave manipulator 2A (Yes), the operation of the actuator 26a of the driving unit 26 which is configured to control the operation of the slave joint portions 24a, 24b for moving the corresponding slave arm 21 is stopped, and the slave joint portions 24a, 24b are switched to a freely operating mode in which the slave joint portions 24a, 24b can be operated manually rather than being operated by the driving unit. At this time, the slave manipulator 2A may announce the switching to the freely operating mode, or output the information to the display apparatus 4 or an audio output device (not shown) to make the information for requesting the authorization to be recognizable by the operator Op.

With regard to the manual operation of the end effector 22, the same process is performed as that of the manual operation of the slave manipulator 2A.

When the manual operation of the slave manipulator 2A by the assistant Ap is finished, the operator Op performs the switching to cause the slave manipulator 2A to switch from the freely operating mode to the driving operation mode in which the slave manipulator 2A is controlled by the driving unit via the operation unit of the master manipulator 3 so as to return to the control method disclosed in the above-described embodiment.

Besides the switching between the freely operating mode and the driving operation mode being controlled by the operation of the operation unit of the master manipulator 3, after the slave manipulator 2A is switched to the freely operating mode, it is possible to perform the process in accordance with Step S1 to Step S9 as shown in FIG. 4 during a predetermined period, and switch back to the driving operation mode once the operation input of the slave manipulator 2A is not detected.

In this modification example, a control mode can be provided such that even in a situation when the blur is determined to be included in the operation input of the slave manipulator 2A, the operation of the slave manipulator 2A can only be controlled by the operation input of the operation unit of the master manipulator 3. According to such a configuration, when the end effector 22 is inserted into the body of the patient P, only the operations by the operator P are reflected such that even if contact with respect to the slave manipulator 2A occurs, the slave manipulator 2A only operates as the operator Op desires. As a result, the malfunction of the manipulator system 1 can be avoided.

According to the modification example, the same as the above-described embodiment, for example, it is possible to prevent unexpected operations of the slave manipulator 2A due to the contact of the adjacent slave manipulators 2 and unintentional contact by the objects and the people surrounding the slave manipulator 2A so as to realize stable operations.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:
1. A medical manipulator system, comprising:
a slave manipulator including an end effector;
a master manipulator configured to receive a manipulation information from an operator;
an actuator configured to generate a driving force for operating the slave manipulator;
a master-manipulator-side sensor disposed at the master manipulator, the master-manipulator-side sensor being configured to detect the manipulation information input to the master manipulator by detecting a movement of the master manipulator, and
a processor comprising hardware, the processor being connected to the master manipulator and the slave manipulator and being configured to:
generate an operating command based on the manipulation information and transmit the operating command to the actuator,
determine whether a blur information due to a shaking of a hand of the operator is included in the manipulation information input to the master manipulator based on a detection result by the master-manipulator-side sensor,
when the blur information is not included in the manipulation information, stop transmitting the operating command to the actuator, and when the blur information is included in the manipulation information, remove the blur information from the manipulation information and generate the operating command based on the manipulation information with the blur information being removed.

2. The medical manipulator system according to claim 1, wherein the slave manipulator further includes:
   a slave arm, the slave arm being configured to hold the end effector, and the slave arm being configured to operate based on the manipulation information input to the master manipulator; and
   a slave-manipulator-side sensor disposed at the slave arm, the slave-manipulator-side sensor being configured to detect the blur information,
   wherein the processor is further configured to:
      switch between a driving mode and a freely moving mode,
      in the driving mode, control an operation of the slave arm by operating the slave arm based on the driving force from the actuator, and
      when the blur information is detected by the slave-manipulator-side sensor, switch from the driving mode to the freely moving mode in which the slave arm is configured to move by being driven by another force except for the driving force.

3. The medical manipulator system according to claim 1, wherein the processor is further configured to:
   include a plurality of control modes, and
   when the blur information is not detected, stop an update of the operating command to the actuator based on a manipulation information from which the blur information is not detected and maintain a current control mode among the plurality of control modes.

4. The medical manipulator system according to claim 1, wherein the processor is further configured to:
   include a plurality of control modes,
   when the blur information is not detected, stop transmitting the operating command to the actuator and prompt the operator to select a next control mode among the plurality of control modes, and
   when the next control mode has been selected and the blur information is detected, switch to the next control mode.

5. The medical manipulator system according to claim 1, wherein the processor is further configured to:
   remove a specified frequency component from an amount of the manipulation information detected by the master-manipulator-side sensor, and
   determine whether the blur information is included by comparing the amount of the manipulation information before removing the specified frequency component and the amount of the manipulation information after removing the specified frequency component.

6. A control method of a medical manipulator system, the medical manipulator system including a slave manipulator having an end effector; a master manipulator receiving a manipulation information from an operator; an actuator generating a driving force for operating the slave manipulator; a master-manipulator-side sensor disposed at the master manipulator and configured to detect the manipulation information input to the master manipulator by detecting a movement of the master manipulator, and a processor comprising hardware, the processor being connected to the master manipulator and the slave manipulator and configured to generate an operating command based on the manipulation information and transmit the operating command to the actuator, the control method comprising:
   determining whether a blur information due to a a shaking of a hand of the operator is included in the manipulation information by the processor;
   stopping transmitting the operating command to the actuator, when the blur information is determined to not to be included in the manipulation information by the processor;
   removing the blur information from the manipulation information by the processor, and
   generating the operating command based on the manipulation information with the blur information being removed, when the blur information is determined to be included in the manipulation information by the processor.

7. The control method of a medical manipulator system according to claim 6, the slave manipulator further comprising a slave arm configured to hold the end effector and operate based on the manipulation information input to the master manipulator; and a slave-manipulator-side sensor disposed at the slave arm and configured to detect the blur information, the control method further including:
   controlling an operation of the slave arm by operating the slave arm based on the driving force from the actuator by the processor, and
   freely moving the slave arm by another force except for the driving force, when the blur information is detected by the slave-manipulator-side sensor by the processor.

8. The control method of a medical manipulator system according to claim 6, further comprising stopping an update of the operating command to the actuator based on a manipulation information from which the blur information is not detected and maintaining a current state of the medical manipulator system by the processor, when the blur information is not detected.

9. The control method of a medical manipulator system according to claim 6, further comprising:
   stopping transmitting the operating command to the actuator, and prompting the operator to select a next step, when the blur information is not detected by the processor, and
   switching to the next step that is selected by the operator, when the blur information is detected after the next step is selected by the processor.

10. The control method of a medical manipulator system according to claim 6, further comprising removing a specified frequency component from an amount of the manipulation information detected by the master-manipulator-side sensor by the processor,
    wherein the determining of whether the blur information is included in the manipulation information is processed by comparing the amount of the manipulation information before removing the specified frequency component and the amount of the manipulation information after removing the specified frequency component.

11. A control device of a medical manipulator system, the medical manipulator system comprising a slave manipulator having an end effector, a master manipulator receiving a manipulation information from an operator, an actuator generating a driving force for operating the slave manipulator, and a master-manipulator-side sensor disposed at the master manipulator and configured to detect the manipulation information input to the master manipulator by detecting a movement of the master manipulator, the control device of the medical manipulator system comprising:
   a processor comprising hardware, the processor being configured to:

generate an operating command based on the manipulation information detected by the master-manipulator-side sensor and transmit the operating command to the actuator of the slave manipulator,
determine whether a blur information due to a shaking of a hand of the operator is included in the manipulation information,
when the blur information is determined not to be included in the manipulation information, stop transmitting the operating command to the actuator, and
when the blur information is determined to be included in the manipulation information, remove the blur information from the manipulation information and generate the operating command based on the manipulation information with the blur information being removed.

* * * * *